(12) United States Patent
Megerle

(10) Patent No.: US 7,183,104 B1
(45) Date of Patent: Feb. 27, 2007

(54) SEPARATOR AND PARTICLE DETECTION SYSTEM

(76) Inventor: Clifford A. Megerle, Lockheed Martin Manassas, 9500 Goodwin Dr., Manassas, VA (US) 20110

(*) Notice: Subject to any disclaimer, the term of this patent is extended or adjusted under 35 U.S.C. 154(b) by 30 days.

(21) Appl. No.: 10/226,702

(22) Filed: Aug. 23, 2002

(51) Int. Cl.
*C12M 1/26* (2006.01)

(52) U.S. Cl. .................. 435/309.1; 422/22; 55/282; 55/307; 209/8; 209/38; 73/863.21; 73/864.71; 95/2; 95/28; 96/2; 96/3; 96/30; 96/31

(58) Field of Classification Search ............ 435/309.1; 422/22, 23; 55/282, 307; 209/8, 38; 73/863.21; 73/864.71; 95/2, 28
See application file for complete search history.

(56) References Cited

U.S. PATENT DOCUMENTS

| | | | |
|---|---|---|---|
| 4,631,124 A * | 12/1986 | Paulson | 209/3 |
| 4,758,267 A * | 7/1988 | Webb | 75/348 |
| 5,125,124 A * | 6/1992 | Saeki et al. | 15/1.51 |
| 5,731,157 A | 3/1998 | Miller et al. | |
| 5,874,046 A | 2/1999 | Megerle | |
| 5,879,549 A | 3/1999 | Caiozza | |
| 6,027,945 A | 2/2000 | Smith et al. | |
| 6,054,324 A * | 4/2000 | Sullivan et al. | 436/174 |
| 6,060,710 A | 5/2000 | Carrieri et al. | |
| 6,194,562 B1 | 2/2001 | Smith et al. | |
| 6,287,781 B1 | 9/2001 | Lee et al. | |
| 6,355,431 B1 | 3/2002 | Chee et al. | |
| 6,368,800 B1 | 4/2002 | Smith et al. | |
| 6,478,856 B1 * | 11/2002 | Leibholz et al. | 95/268 |
| 6,490,530 B1 * | 12/2002 | Wyatt | 702/24 |
| 6,729,196 B2 * | 5/2004 | Moler et al. | 73/863.22 |
| 6,743,365 B1 * | 6/2004 | Marlowe | 210/695 |
| 2001/0029793 A1 | 10/2001 | Moler et al. | |
| 2002/0053283 A1 | 5/2002 | Akyildiz | |

FOREIGN PATENT DOCUMENTS

| | | |
|---|---|---|
| EP | 1 158 292 A2 | 11/2001 |
| JP | 404027450 A * | 1/1992 |
| WO | WO 99/09042 | 2/1999 |
| WO | WO 99/34401 | 7/1999 |
| WO | WO 99/47255 | 9/1999 |
| WO | WO 02/33764 A2 | 4/2002 |

OTHER PUBLICATIONS

Richard H. Tullis, Ultrasensitive Nonradioactive Detection of PCR Reactions: An Overview, The Polymerase Chair Reaction, Mullis et al. Editors, 1994, 124-125, Birkhauser, Boston, USA.
Gregory S. Makowski, PH.D., Esther L. Davis, M.T. (ASCP), and Sidney M. Hopper, PH.D., The Effect of Storage on Guthrie Cards: Implications for Deoxyribonucleic Acid Amplification, Annals of Clinical and Laboratory Science, 1996, pp. 458-469, vol. 26, No. 5., Institute.
L.E. Bockstahler, G.L. Johnson, and R. Berko, Polymerase Chain Reaction (PCR) Detection of Microbacterium tuberculosis (Mtb) Inhibited by Iron, C-330, Center for Devices and Radiological Health, U.S. FDA (HFZ-113), Rockville, MD.
Christopher Aston, Biological Warfare Canaries, IEEE Spectrum, Oct. 2001, vol. 38, No. 10, IEEE.
Yu-Li Tsai and Betty H. Olson, Detection of Low Numbers of Bacterial Cells in Soils and Sediments by Polymerase Chain Reaction, Applied and Environmental Microbiology, Feb. 1992, p. 754-757, American Society for Microbiology.

* cited by examiner

*Primary Examiner*—David Redding

(57) ABSTRACT

The present invention is embodied in a system for collecting biological samples from air including a collection assembly to store at least one biological sample and a separator to remove selected particles from the air prior to entry into the collection assembly. In one embodiment, the selected particles are magnetic and the separator includes at least one magnet to attract the particles from the air.

14 Claims, 7 Drawing Sheets

SEPARATOR AND PARTICLE DETECTION SYSTEM

BACKGROUND OF THE INVENTION

1. Field of the Invention

Figure 1:
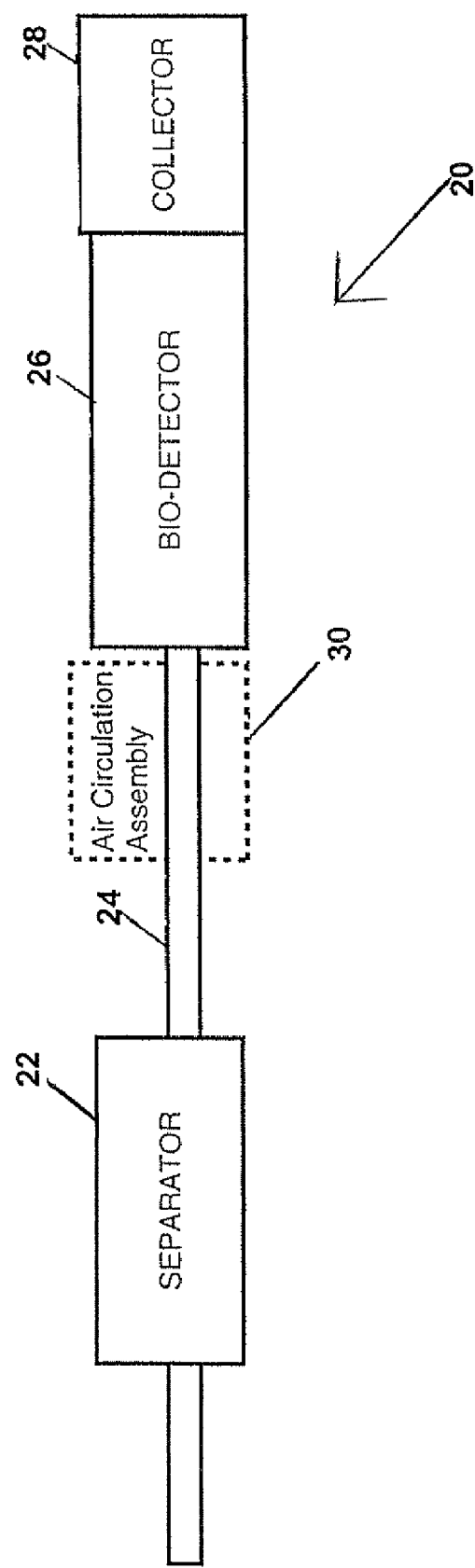
Figure 2:
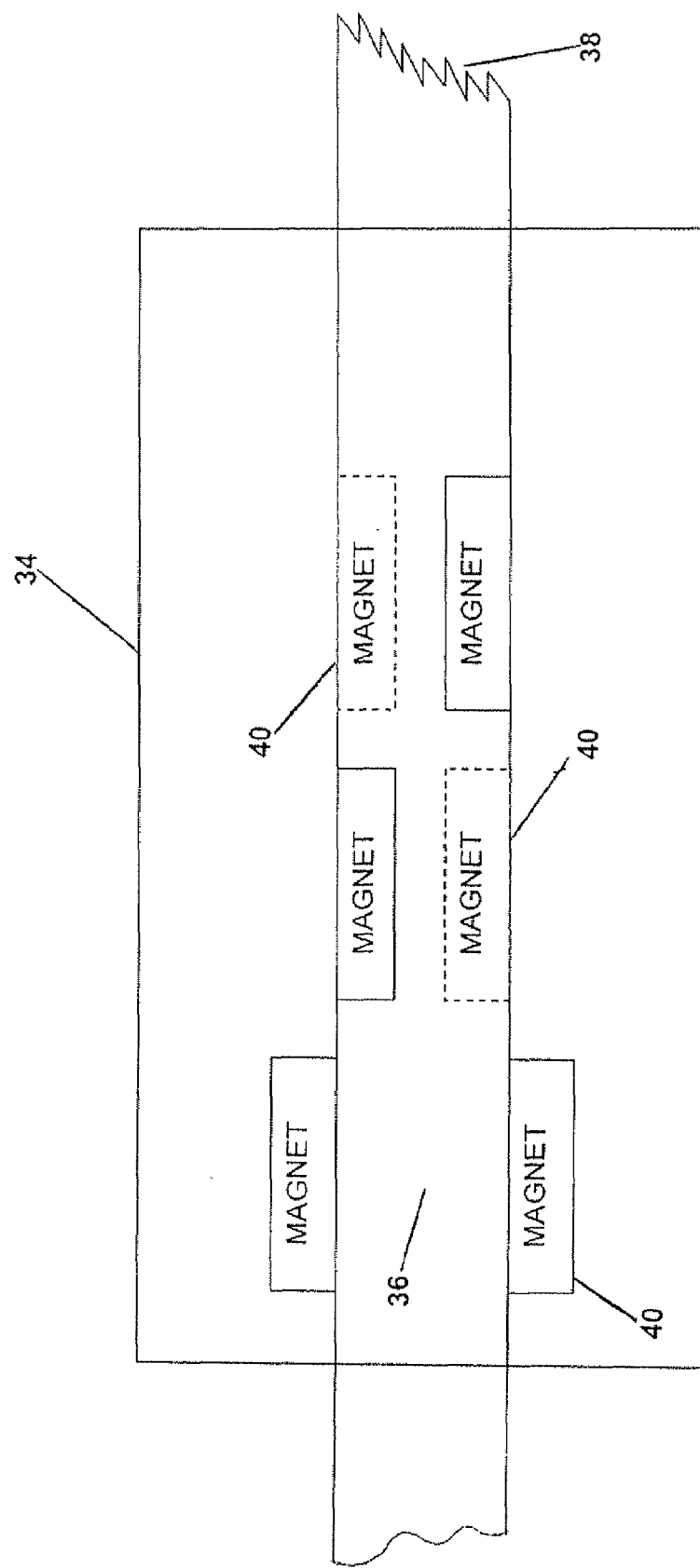
Figure 3:
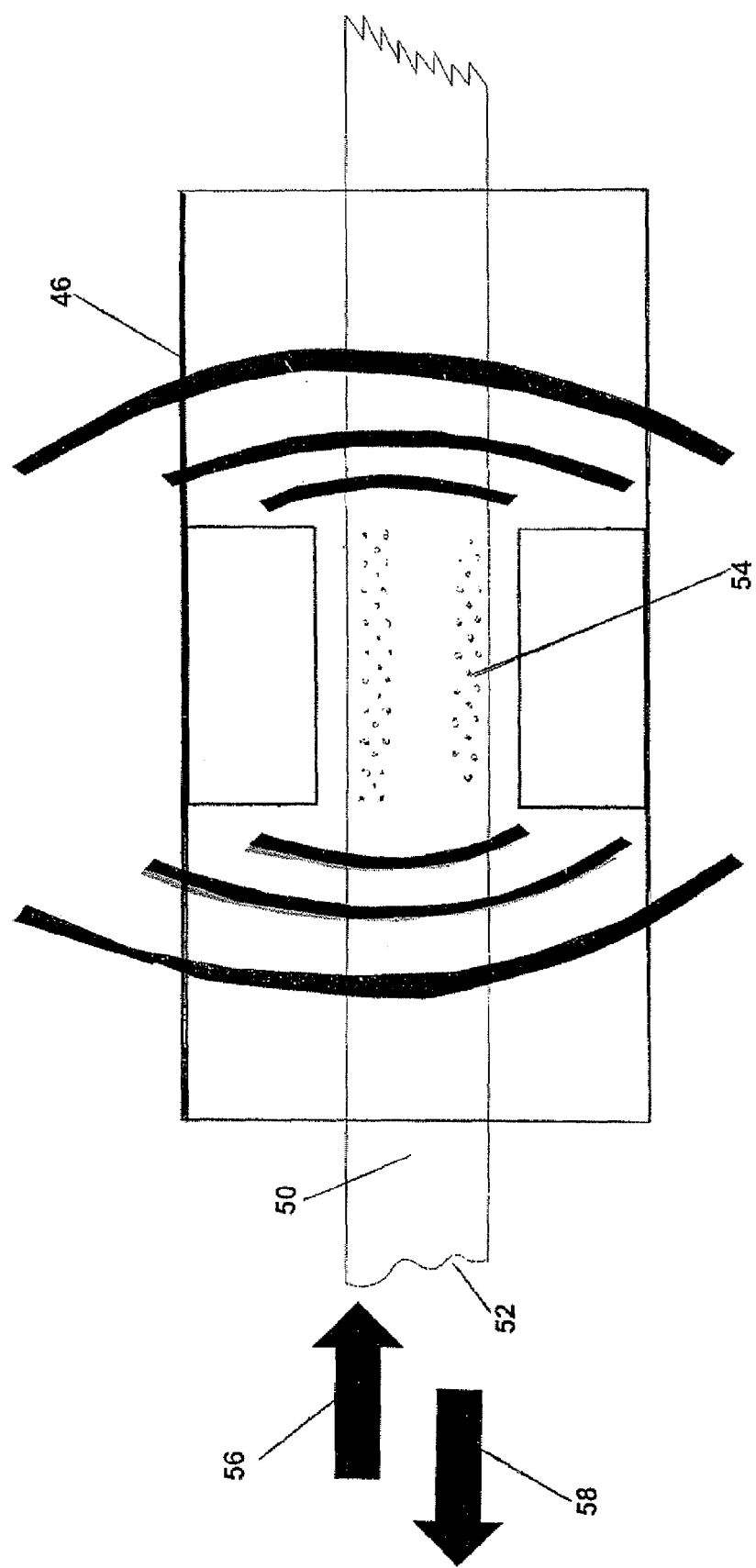
Figure 4:
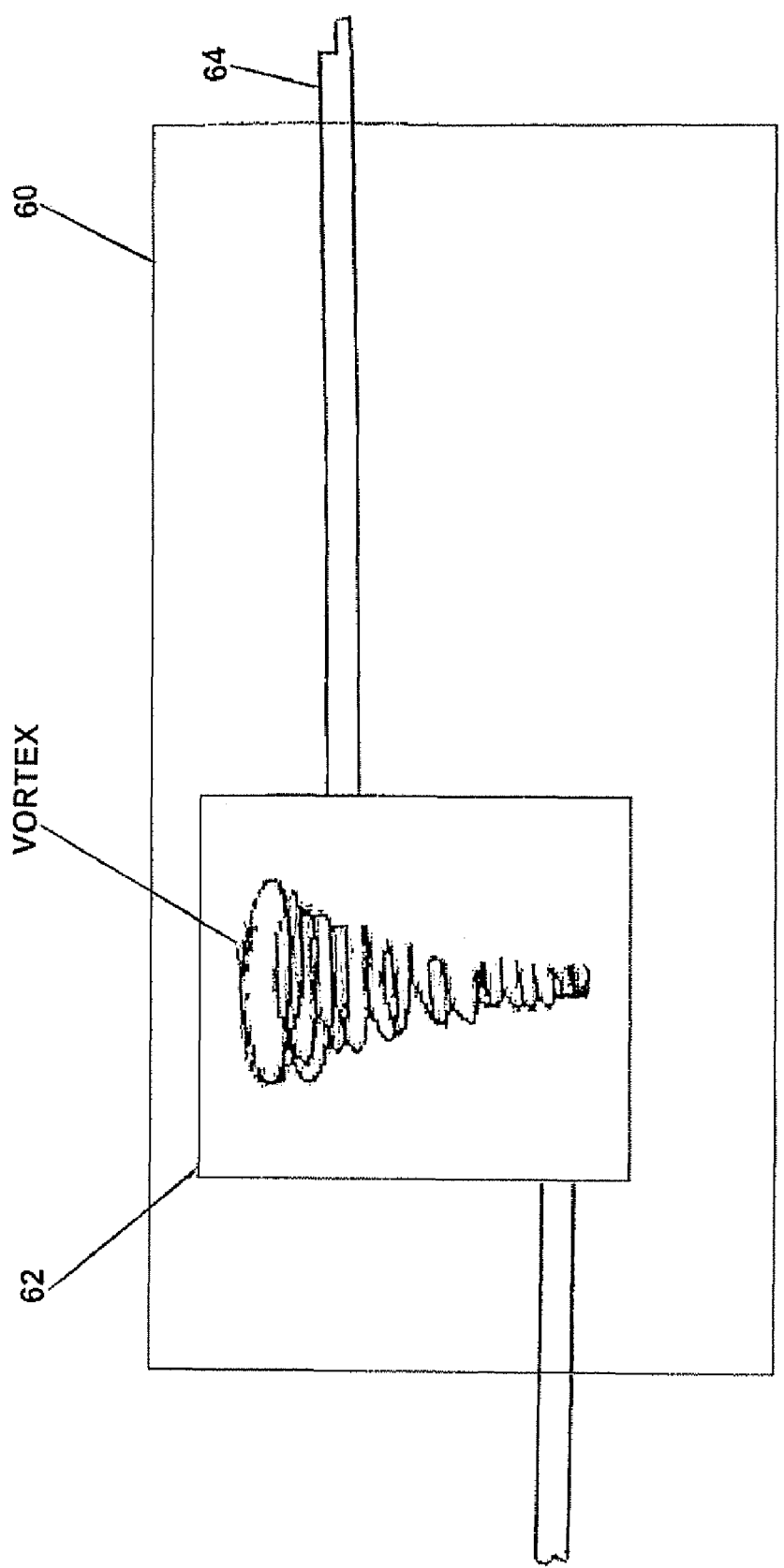
Figure 5:
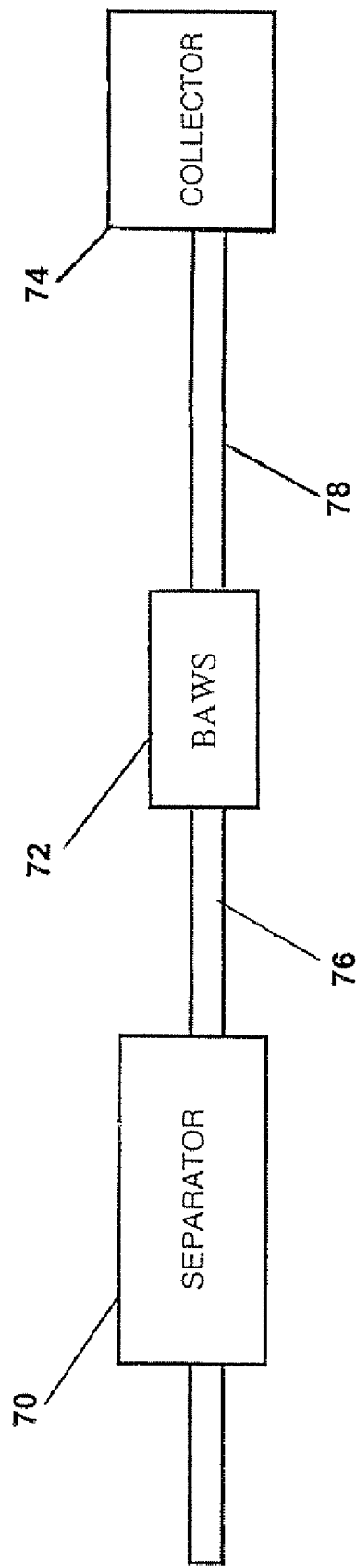
Figure 6:
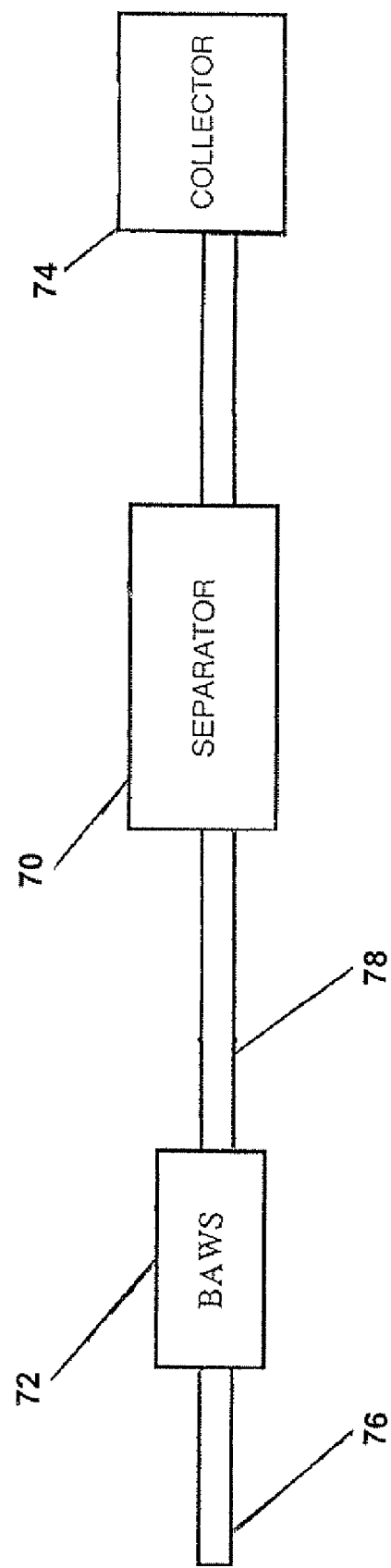
Figure 7:
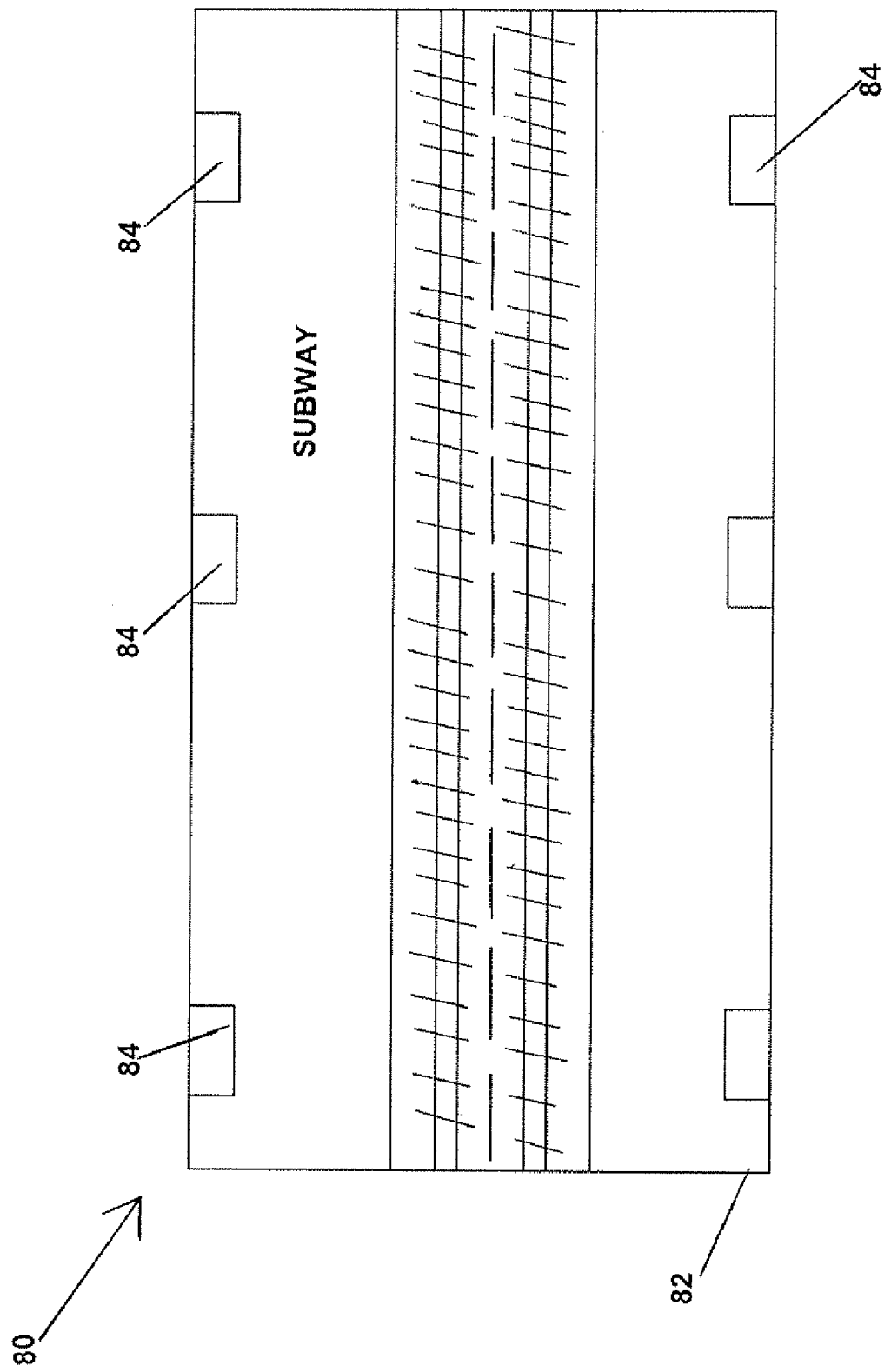

The present invention relates to bioparticle detectors and more particularly to separators for use with bioparticle detectors.

2. Description of the Related Art

Having breathable air is something that most people take for granted and little thought is often provided as to the contents of the air when entering a building or taking public transportation. In fact people take it for granted that the air delivered in a building, on an airplane or in a subway will be generally free from harmful airborne debris.

Recently, however, people have become aware that the air may be easily poisoned through the introduction of chemical or biological material into the air. The vulnerability of the air in controlled environments was exemplified when Anthrax was recently distributed through the mail resulting in the illness and death of several postal workers.

Presently, the military uses sophisticated chemical and biological detectors on the battlefield to provide early detection to the introduction of chemical and/or biological weapons into the battlefield environment. With the recent realization that these same weapons can be used by terrorists to cause harm to people in any public place, the focus and use of chemical and biological weapon detection devices has shifted away from the outdoor environments of the battlefield to enclosed metropolitan environments.

Devices for detecting harmful biological material in the air, biodetectors, are being developed in three broad classes of systems:

1. Systems that detect the organism or molecule by sensing the presence of a DNA sequence, protein or other antigen that is characteristic of the bioagent through its interaction with a test molecule.

2. Biological tissue-based systems, in which a bioagent or bio-toxin affects live mammalian cells resulting in a measurable response.

3. Chemical mass spectrometry systems that break the samples down into component molecular fragments and compares mass fragmentation patterns with those of bioagents and other molecules.

In the field, biodetectors are presently available in two forms, namely, devices that merely collect samples for analysis at a laboratory using one of the above methodologies and devices capable of collecting samples and testing the samples on-site for the presence of harmful biological material. In either case, it is desirable to retain samples of the biological material for later testing and study. One drawback to the biodetection process is that the sample collected may contain a small number of the biological organisms. The biological organisms may be identified by the presence and detection of ribonucleic acid (RNA) and deoxyribonucleic acid (DNA) sequences. Even though only a small sample may actually be collected, samples of RNA and DNA may be copied to increase the sample size through a process known as Polymerase Chain Reaction (PCR). One drawback to the PCR process is that the process is inhibited or will not work when iron is present in the sample. Thus, it is desirable to collect samples of biological material that are relatively free of iron. In current outdoor applications for biodetectors, the amount of iron or other inhibitors present in such environments has not been considered sufficient to effect the samples collected.

Traditionally, biodetectors were designed to be placed in outdoor battlefield environments. With the use of biodetectors in enclosed urban environments air circulation and unusual sources may increase the concentration of inhibitors in the air and, thus, the need exists for ways to adapt the biodetectors for indoor use in urban environments.

SUMMARY OF THE INVENTION

The present invention is embodied in a system for collecting biological samples from air including a collection assembly to store at least one biological sample and a separator to remove selected particles from the air prior to entry into the collection assembly.

In one embodiment, the selected particles are magnetic and the separator includes at least one magnet to attract the particles from the air.

BRIEF DESCRIPTION OF THE DRAWINGS

FIG. 1 is a block diagram of a separator and biodetector according to an embodiment of the present invention.

FIG. 2 is an embodiment of a magnetic separator.

FIG. 3 is another embodiment of a magnetic separator.

FIG. 4 is an embodiment of a non-magnetic separator.

FIG. 5 is a block diagram of a biodetector and separator assembly.

FIG. 6 is a block diagram of a biodetector and separator assembly.

FIG. 7 is a diagram of a biodetector system.

DETAILED DESCRIPTION OF THE PREFERRED EMBODIMENT(S)

The present invention relates to a system for detecting biological materials in the air of a closed urban environment such as subways, train stations and office buildings. The present invention is based upon the realization and discovery that certain urban environments may cause artificial concentrations of iron or other inhibitors to the biodetection process in the air. In the case of a subway system, the existence of steel rails, wheels, iron drums and rotors, and iron-containing pads in the brakes of the subway cars, can cause high concentrations of aerosolized iron particles in subway air. While these particles are not generally considered to be a health threat to the public, the presence of these particles can affect the ability to use PCR on samples collected by a biodetector. Advantageously, the present invention utilizes a separator to remove such inhibitors from samples before they are collected. By utilizing a separator to remove iron and other inhibitors, the polynucleic acids in the sampled organisms may be copied and increased/amplified using PCR.

With reference to the drawings for purposes of illustration, a particle detector 20 (FIG. 1) according to an embodiment of the present invention includes a separator 22 connected to the air intake 24 of a biodetector 26 having a sample collector 28. The separator 22 may be housed within the biodetector assembly (not shown) or included along the air intake 24 as illustrated in FIG. 1. Presently, collectors for obtaining samples may store samples on filter paper in an aqueous solution, on growth media, on tape, solid substrates, on other solid supports or media, or in other liquids. The use of a separator 22 prior to storage of the samples in a collector 28 is preferred as the processes of separation are made more difficult once the sample has been stored in the collector. A conventional biodetector device may include an air circulation assembly 30 for drawing in air samples and optionally reversing the air flow periodically to flush out the system. The biodetector operates to direct the air sampled to the collector. The biodetector may also operate passively if located in an area with sufficient air flow. The samples in the collector may then be collected for off-site analysis or some devices may include the ability to analyze the sample on site. Automated analysis devices of the type suitable for this purpose include devices manufactured by Cepheid Corporation of Sunnyvale, Calif. and such device sold under the brand names "Smart Cycler" and "GeneXpert". Another is manufactured by Idaho Technology of Salt Lake City, Utah, and sold under the brand name "R.A.P.I.D."

In the case of materials containing iron, the separator operates to separate out iron containing particles from the air sample while allowing the biological materials to pass through to the collector. In distinguishing between the biological material and iron containing material, there are two features that are useful. First it recognized that the iron containing materials have magnetic properties. Thus, the separator may use magnetic fields to draw magnetic particles out of the air flow before they can reach the collector. Other magnetic contaminants would also be removed, while non-magnetic biological materials would pass through the separator to the collector or bio-detector and would be unaffected by its presence.

In addition, it is recognized the biological materials are generally found in the range of 2–10 microns (μm) in diameter and is believed to be generally lighter in weight and less dense than iron containing particles. Thus, a vortex may be used to separate out the heavier particles from the air stream before the air sample reaches the collector.

With reference to FIG. 2, an example of a magnetic separator 34 is coupled to the outside surface 36 of an air intake pipe 38 for a biodetector (not shown). A plurality of magnets 40 are distributed about the outer surface to provide varying magnetic fields that operate collectively to draw magnetic particles out of the air flow and which are held in place by the magnetic field created by the magnets. The magnets can either be in the form of electro-magnets in which the magnetic field would require a charge or the magnetic field could be provided by natural magnets. The number of magnets used (e.g. one or more) and distribution along the air intake would depend on factors such as the air flow rate, the magnetic field strength in relation to the air flow rate, the diameter of the pipe and the sensitivity of the biodetector equipment to magnetic fields. As air is drawn into the biodetector, the magnetic separator operates to attract iron particles towards the polar ends of the magnetic fields. Periodically, the air intake needs to be cleaned and is accomplished by manually cleaning of the air intake with a pipe cleaner or the like.

With reference to FIG. 3, a magnetic separator 46 is shown having an electro magnet 48 attached to the outside surface 50 of the air intake pipe 52. The electro-magnet draws iron and other magnetic particles 54 to the inner wall of the air intake pipe as the air flows in as represented by line 56. Periodically, the air flow may be reversed to flush out the system, whereby a burst of air is pumped out of the pipe as represented by line 58. At that moment the electromagnet may be switched off and the particles 54 along the inner wall, no longer held by the magnet, are flushed out of the air intake and away from the collector. In this way, the separator may be incorporated with a self cleaning mode. Such a device could also be cleaned manually.

With reference to FIG. 4, a non-magnetic separator 60 is shown having a vortex generator 62 created along the air intake pathway 64 of the biodetector. As discussed above, the vortex separates out the heavier particles from the air sample and allows the lighter particles to pass through the air intake into the collector.

In another embodiment (FIGS. 5 and 6), the separator 70 may be included with a biodetector incorporating a Bio Aerosol Warning System (BAWS) 72 that includes an optical counter to detect particles entering the collector 74. The separator 70 may be included either along the air intake 76 or exhaust 78 of the BAWS 72 as the order of these two devices does not matter. One such system is manufactured by the Lockheed Martin Corporation which can be used as a stand-alone, remotely-placed device, or as part of a larger, integrated system of BAWS units. With reference to FIG. 7, a network system 80 is shown in a subway station 82 in which a pluralty of biodetector devices 84 fitted with a separator are distributed throughout the subway station 82. The actual placement of the detector would depend on factors such as the configuration of the airducts and passageways.

It should be noted that the separators as presently described may be used in a variety of configurations that may include biodetectors or biocollectors in combination with passive and forced-air air circulation systems. Thus, the combinations of detectors and biocollectors described above are intended to be exemplary, not limiting.

While the present invention has been described in connection with what are presently considered to be the most practical and preferred embodiments, it is to be understood that the invention is not to be limited to the disclosed embodiments, but to the contrary, is intended to cover various modifications and equivalent arrangements included within the spirit of the invention, which are set forth in the appended claims, and which scope is to be accorded the broadest interpretation so as to encompass all such modifications and equivalent structures.

What is claimed is:

1. A system for collecting biological samples from air comprising:

a collection assembly to store at least one biological sample;

an air intake assembly to draw air into the collection assembly and to reverse airflow to flush out the system;

a separator to attract and remove magnetic particles from said air prior to entry into said collection assembly; and means for synchronously switching said separator from an active state to an inactive state when said airflow direction is changed.

2. The system of claim 1 wherein said magnetic particles include iron and said separator includes at least one magnet positioned along said air intake assembly to cause said particles to move traversely with regard to air flow.

3. The system of claim 2 wherein said separator is magnetic.

4. The system of claim 3 wherein said separator is electromagnetic.

5. The system of clam 3 wherein said separator includes at least one natural magnet.

6. The system of claim 1 wherein said separator is positioned along said air intake assembly.

7. The system of claim 6 wherein said electromagnet is charged to produce a magnetic field that attracts said particles traverse to air flow in said air intake assembly.

8. The system of claim 6 wherein said electromagnet is switchable to an off state.

9. The system of claim 1 wherein said collection assembly includes a container to store biological material.

10. The system of claim 1 wherein said collection assembly includes filter paper to capture biological material.

11. A system for collecting biological samples from air comprising:
- a collection assembly to store at least one biological sample, said collection assembly including a liquid solution to store biological material;
- an air intake assembly to draw air into the collection assembly; and
- a separator to attract and remove magnetic particles from said air prior to entry into said collection assembly.

12. The system of claim 1 wherein said collection assembly includes a tape to store biological material.

13. A system for collecting biological samples from air comprising:
- a collection assembly to store at least one biological sample, said collection assembly including a growth media to store biological material;
- an air intake assembly to draw air into the collection assembly; and
- a separator to attract and remove magnetic particles from said air prior to entry into said collection assembly.

14. The system of claim 1 wherein said collection assembly includes a solid substrate to store biological material.

* * * * *

UNITED STATES PATENT AND TRADEMARK OFFICE
CERTIFICATE OF CORRECTION

PATENT NO.       : 7,183,104 B1                                    Page 1 of 1
APPLICATION NO.  : 10/226702
DATED            : February 27, 2007
INVENTOR(S)      : Clifford A. Megerle It is certified that error appears in the above-identified patent and that said Letters Patent is hereby corrected as shown below:

Item No. (76) is entered as "Clifford A. Megerle, Lockheed Martin Manassas, 9500 Goodwin Dr., Manassas, VA (US) 20110", please enter Item No. (76) as follows:

Clifford A. Megerle, Thousand Oaks, CA 20110

Item No. (73) does not appear. Please enter Item No. (73) as follows:

(73) Assignee: Lockheed Martin Corporation, Bethesda, Maryland

Item No. (74) does not appear. Please enter Item No. (74) as follows:

(74) Attorney, Agent, or Firm - Duane Morris LLP

Signed and Sealed this

First Day of May, 2007

JON W. DUDAS
*Director of the United States Patent and Trademark Office*